US011111362B2

(12) United States Patent
Zhang et al.

(10) Patent No.: US 11,111,362 B2
(45) Date of Patent: Sep. 7, 2021

(54) BREATHABLE FILMS WITH MICROBIAL BARRIER PROPERTIES

(71) Applicant: Becton, Dickinson and Company, Franklin Lakes, NJ (US)

(72) Inventors: Jianbin Zhang, Livingston, NJ (US); Theresa Hermel-Davidock, Newton, NJ (US); Edward Bryan Coughlin, Amherst, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 51 days.

(21) Appl. No.: 15/711,653

(22) Filed: Sep. 21, 2017

(65) Prior Publication Data

US 2018/0086903 A1    Mar. 29, 2018

Related U.S. Application Data

(60) Provisional application No. 62/399,743, filed on Sep. 26, 2016.

(51) Int. Cl.
| | |
|---|---|
| *C08L 23/06* | (2006.01) |
| *A61L 15/22* | (2006.01) |
| *A61L 26/00* | (2006.01) |
| *C08F 210/02* | (2006.01) |
| *C08F 218/08* | (2006.01) |
| *C08L 51/08* | (2006.01) |
| *A61L 15/00* | (2006.01) |
| *C08F 255/02* | (2006.01) |
| *C08J 5/18* | (2006.01) |
| *C08L 71/02* | (2006.01) |

(52) U.S. Cl.
CPC .............. *C08L 23/06* (2013.01); *A61L 15/00* (2013.01); *A61L 15/225* (2013.01); *A61L 26/0052* (2013.01); *C08F 210/02* (2013.01); *C08F 218/08* (2013.01); *C08F 255/02* (2013.01); *C08J 5/18* (2013.01); *C08L 51/08* (2013.01); *C08L 71/02* (2013.01); *C08J 2323/08* (2013.01); *C08J 2451/06* (2013.01); *C08J 2471/02* (2013.01); *C08L 2203/02* (2013.01); *C08L 2203/16* (2013.01)

(58) Field of Classification Search
CPC ...... C08L 23/06; C08L 71/02; C08L 2203/02; C08L 51/08; A61L 15/225; A61L 26/0052
See application file for complete search history.

(56) References Cited

U.S. PATENT DOCUMENTS

| | | | |
|---|---|---|---|
| 3,029,216 A | 4/1962 | Bailey, Jr. et al. | |
| 3,978,855 A | 9/1976 | McRae | |
| 4,727,120 A | 2/1988 | Nogues | |
| 4,960,594 A | 10/1990 | Honeycutt | |
| 5,214,091 A | 5/1993 | Tanaka et al. | |
| 5,292,803 A | 3/1994 | Ohmae et al. | |
| 5,424,150 A | 6/1995 | Ohnishi et al. | |
| 6,433,080 B1 | 8/2002 | Fujiki et al. | |
| 6,613,187 B1 | 9/2003 | Ding et al. | |
| 6,649,681 B2 | 11/2003 | Rohn et al. | |
| 6,673,192 B1 | 1/2004 | Woods et al. | |
| 8,722,962 B2 | 5/2014 | Dera et al. | |
| 9,150,674 B2 | 10/2015 | Hermel-Davidock et al. | |
| 2004/0034184 A1 | 2/2004 | Takashima et al. | |
| 2008/0273820 A1 | 11/2008 | Wiker et al. | |
| 2010/0111167 A1 | 5/2010 | Wu et al. | |
| 2010/0303891 A1 | 12/2010 | Lee et al. | |
| 2012/0005930 A1 | 1/2012 | Cragg | |
| 2013/0189340 A1* | 7/2013 | Kim ...................... A61L 27/34 424/423 |
| 2014/0058045 A1 | 2/2014 | Hermel-Davidock et al. | |
| 2015/0018791 A1 | 1/2015 | Devenish et al. | |
| 2015/0166706 A1* | 6/2015 | Hrabie .................. C08F 226/10 424/78.24 |

FOREIGN PATENT DOCUMENTS

| | | |
|---|---|---|
| CA | 2383117 A1 | 3/2001 |
| CN | 101055422 A | 10/2007 |
| JP | 50-112494 A | 9/1975 |
| JP | H04-94725 A | 3/1992 |
| JP | 5232796 B2 | 7/2013 |
| WO | 87/05206 A1 | 9/1987 |
| WO | 01/18112 A2 | 3/2001 |
| WO | 2014/159419 A1 | 10/2014 |
| WO | 2015/032817 A1 | 3/2015 |

OTHER PUBLICATIONS

Parzuchowski, Pawel G. et al., J. Am. Chem. Soc. 2002, 124, pp. 12182-12191 (Year: 2002).*
Database WPI, Week 199219, Mar. 26, 1992, Thomson Scientific, London, GB; AN 1992-156090, XP-002775754.
PCT International Search Report and Written Opinion in PCT/US2017/052927 dated Nov. 29, 2017, 14 pages.
Lu, et al., "Synthesis of graft copolymer polyethylene-graft-poly(ethylene oxide) by a new anionic graft-from polymerization", Polymer International, vol. 53, No. 12, Dec. 31, 2004, pp. 1963-1967.
SciFinder search, American Chemical Society, 2015, 20 pages.
Pebax in Medical Applications, 2 pgs.
(Continued)

*Primary Examiner* — Andrew S Rosenthal
*Assistant Examiner* — Lyndsey M Beckhardt
(74) *Attorney, Agent, or Firm* — Servilla Whitney LLC (57) ABSTRACT

Films for medical devices and/or packaging include polyethylene-poly(ethylene oxide) amphiphilic graft copolymers (PE-g-PEO) in their base polymer formulations of polyethylene and poly(ethylene oxide). The films may be treated to include a nitric-oxide releasing agent incorporated into the PE-g-PEO. Also, microbial agents for inclusion in medical devices are provided, which comprise: an olefin-poly(ethylene oxide) amphiphilic graft copolymer, wherein a portion of the poly(ethylene oxide) comprises end groups converted to a nitric oxide-releasing agent. The amphiphilic graft copolymer of the microbial agents may comprise a polyethylene-poly(ethylene oxide) amphiphilic graft copolymer (PE-g-PEO), a polypropylene-poly(ethylene oxide) amphiphilic graft copolymer (PP-g-PEO), or mixtures thereof.

19 Claims, 3 Drawing Sheets

(56) References Cited

OTHER PUBLICATIONS

Chen, et al., "Break-Through in Breathable Polymers: Morphology, Properties, and Performance", Dupont, Wilmington, DE, 1-8.

Gugliuzza, et al., "Role of additives in the water vapor transport through block co-poly(amide/ether) membranes: effects on surface and bulk polymer properties", European Polymer Journal 40, 2004, 2381-2389.

Jeon, et al., "Premade vs. reactively formed compatibilizers for PMMA/PS melt blends", Polymer 46, (2005), 12422-12429.

Johnson, et al., "Breathable TPE Films for Medical Applications", MDDI Medical Device and Diagnostic Industry News Products and Suppliers, Jul. 2000, 6 pages.

Jones, et al., "Antimicrobial properties of nitric oxide and its application in antimicrobial formulations and medical devices", Appl Microbial Biotechnol (2010), 88: 401-407.

Jonquieres, et al., "Permeability of block copolymers to vapors and liquids", Prog. Polym. Sci. 27, 2002, 1803-1877.

Lowe, et al., "Electrospun nitric oxide releasing bandage with enhanced wound healing", Acta Biomaterialia 13 (2015), 121-130.

Metz, et al., "Gas-Permeation Properties of Poly(ethylene oxide) Poly(butylene terephthalate) Block Copolymers", Macromolecules 37, 2004, 4590-4597.

Metz, et al., "Water vapor and gas transport through a poly(butylene terephthalate) poly(ethylene oxide) block copolymer", Desalination 148, 2002, 303-307.

Mueller, et al., "Breathable Polymer Films Produced by the Microlayer Coextrusion Process", Journal of Applied Polymer Science, vol. 78, 2000, 816-828.

Nandi, et al., "Open-pore morphology of i-PP copolymer crystallized from a gel state in supercritical propane", Polymer 45, 2004, 4819-4827.

Seabra, et al., "Polynitrosated Polyesters: Preparation, Characterization, and Potential Use for Topical Nitric Oxide Release", Biomacromolecules 2005, 6, 2512-2520.

Sirkar, "Membranes, Phase Interfaces, and Separations: Novel Techniques and Membranes—An Overview", Ind. Eng. Chem. Res. 47, 2008, 5250-5266.

Winter, et al., "Rigid Pore Structure from Highly Swollen Polymer Gels", Macromolecules 35, 2002, 3325-3327.

\* cited by examiner

FIG. 3
REFERENCE

BREATHABLE FILMS WITH MICROBIAL BARRIER PROPERTIES

CROSS-REFERENCE TO RELATED APPLICATIONS

This application claims priority to U.S. Provisional Application No. 62/399,743, filed Sep. 26, 2016, the entire disclosure of which is hereby incorporated by reference herein.

TECHNICAL FIELD

Principles and embodiments of the present invention relate generally to films including polyethylene-poly(ethylene oxide) amphiphilic graft copolymers (PE-g-PEO) in their base polymer formulations. Specifically, films that are formed from formulations of polyethylene and poly(ethylene oxide) including PE-g-PEO provide both breathability and a microbial barrier. Also, microbial agents for inclusion in medical devices are provided, which comprise: an olefin-poly(ethylene oxide) amphiphilic graft copolymer, wherein a portion of the poly(ethylene oxide) comprises end groups converted to a nitric oxide-releasing agent.

BACKGROUND

Polyethylene (PE) is one of the most widely used polymeric materials globally. Linear low density polyethylene (LLDPE) in particular is used in a broad range of film applications, from agricultural films, saran wrap, and bubble wrap, to multilayer and composite films. It has also been used in the medical device industry, is recyclable, and is considered one of the "greenest" petroleum-derived polymeric systems by non-governmental organizations (NGOs).

Most of the polyethylene film used on the market is made of blown film. PE films have excellent toughness, flexibility and relative transparency. PE films, however, are not breathable. PE is extremely hydrophobic. To make a PE film surface hydrophilic, a hydrophilic coating may be applied, but the process is not trivial. Controlling performance of the coating is also a challenge due to the poor binding strength often seen between PE and the coating materials.

With respect to medical packaging, beyond the United States and European countries, radiation based sterilization techniques are not readily available and ethylene oxide (EtO) sterilization is the primary mode used. A breathable package is needed for EtO sterilization. Additionally, non-breathable film-film packages are currently limited to the geographical markets they can be sold to due to the limitations of the altitude the package can experience without incurring open seals. At high altitudes the air within the non-breathable package expands and can cause open seals, loss of sterility of the product, and ultimately resulting in product recalls. Paper top webs are common alternatives used, but they usually require an adhesive coating which increases the cost. Additionally, paper is susceptible to tearing and punctures, which can result in loss of sterility of the product, and recalls. Direct seal paper, paper without an adhesive coating, while low cost, is difficult to run on current packaging machines, can have a narrow seal performance window between weak, open seal or strong seal which result in fiber tear or tearing of the paper. Both the weak seal and paper tears compromise the sterility of the product. Breathable non-paper films, such as Tyvek®, can be used but they are substantially more costly than conventional films. PEBAX® are commercially available polyamide/polymer ether copolymers which offer breathability, steam sterilization capabilities while maintaining a sterile barrier. Like Tyvek, these are specialized and expensive materials. These films are more elastomeric in nature and would not be applicable to top webs for primary packaging of medical devices.

An approach to achieving breathability of a polymeric film is the concept of micro-perforated films, which is utilized in a wide variety of commercial applications, commonly in food packaging and medical & health. The food packaging applications primarily apply to fresh product wrapping to enhance shelf life, but are also used in wrapping things such as fresh breads and other baked goods. These micro-perforated films are tailored to have very selective permeation rates to oxygen, carbon dioxide, and moisture. The low moisture vapor transmission rate (MVTR) preserves the moisture of the produce and extends its sellable shelf life. Alternatively, perforated films are also used in medical and health applications. These films typically have larger perforations and have very high MVTR, and resulting poor physical properties. These films include applications like breathable sheets for diapers and feminine hygiene products. They are also used in wound dressings, exam and surgery room paper, and the like. These films would not have the proper breathability while maintaining both a microbial barrier and the required physical properties for primary packaging of medical devices.

Another approach to achieving breathability is the use of rigid fillers, such as talc, and applying a post-fabrication stretching to the film. This result in a film will poor structural integrity, with pores which would not maintain a microbial barrier, and the residual rigid filler would contaminate the medial device within the package.

With respect to wound dressings, wounds affect millions of people's lives in the world, either acute or chronic. The repair process for acute wound involves four phases including coagulation, inflammation, formation of granulation tissue, and scar formation. For chronic wounds, either vascular, diabetic or pressure ulcers, it involves a prolonged inflammatory phase, persistent infections or inability for reparatory stimuli. Dressing is applied to a wound to prevent further damage and to promote the healing process.

Typically a wound dressing is in direct contact with skins or wounds, focusing towards promoting recovery and preventing further damage, regardless of the type of wound (acute or chronic), severity, or location of the wounds (skin, vascular, or else). Attributes of a wound dressing include: stop bleeding, to seal the wound to expedite the clotting process; absorb exudate to transport/absorb fluid discharges like blood, plasma, body fluids, and the like; infection prevention to provide a physical barrier to protect the wound against germs, bacteria, or mechanical damages; debride the wound to remove slough or foreign matters from the wound; moisture adjustment to control the moisture so that the wound could stay moist or dry; promote healing to contribute to recovery via granulation and epithelialization.

Wound dressings desirably have the following physical/mechanical/biological properties: mechanical strength; permeable to gas/liquid; barrier properties against germs, bacteria, and the like; moisture maintaining properties; biocompatibility. A common approach to fulfill all the properties is by combining layers of different materials or designs, with each component providing one or two individual property/function. A wound dressing can be a complex device, with a functional layer which typically provides some liquid/gas permeability and bacteria barrier properties, a carrier layer which provides the mechanical performance and the integrity of the dressing, and an adhesive layer in between to hold the functional layer and the carrier layer together. For example, a wound dressing composite can comprise a functional polyurethane film, which provides permeability and some bacteria barrier properties, an adhesive layer (could be hypoallergenic acrylate copolymer), and a relatively stiff substantially transparent integral film carrier sheet, which can be polyethylene. The functional polyurethane film is not strong enough to hold its shape or keep its integrity. A carrier layer, however, desirably is able to function as a wound dressing.

For the stimulation of healing, suitable moisture is needed. For example, hydrogels like poly(ethylene oxide) or poly(ethylene glycol), foams, hydrocolloids, cellulose, polyurethane films and etc. have been used for this purpose, called passive wound dressing. Such materials can provide useful properties: protect peri-wound skin, maintain a suitable moisture level, and prevent biofilm formation. Many synthetic polymers have been used for this purpose, for example, polyethylene glycol-gelatin based semi-interpenetrating network, polyvinyl alcohol-gelatin esterified hydrogel, polyvinyl alcohol and polyacrylic acid based hydrogel, and etc. A limitation of hydrogel types of materials is mechanical strength. Most of such materials have poor mechanical properties and thus a substrate or a carrier is used for mechanical integrity.

Another group of permeable film often used in wound dressing is non-woven polymer films. Through electrospinning, polymers can form micro/nano-scale fibers and then a non-woven film. Many materials have been made into films through this process, for example polylactide, polyglycolic acid, polyacrylic acid, polycaprolactone, polyethylene glycol, polyurethane, and etc. Good mechanical performance may be achieved by these materials, however, moisture control likely becomes a tradeoff, or vice versa.

There is a continuing need to prepare breathable films for the medical industry. There is a need for a commodity resin based top web film, which would allow for EtO sterilization and global sale capability. There is also a need for medical films having robust physical and processing properties to meet a broad spectrum of packaging lines and products. There are also needs for wound dressing films that meet breathability, moisture, and microbial barrier criteria. There are also needs for providing wound dressing films that provide continuous antimicrobial protection and wound healing promotion.

SUMMARY

Provided are films providing both breathability and microbial barrier. By incorporating polyethylene-poly(ethylene oxide) amphiphilic graft copolymer (PE-g-PEO) into PE films with free poly(ethylene oxide) PEO, a breathable and microbial barrier PE film can be manufactured with commercial grade PE via conventional film processes such as cast extrusion and potentially blown film conversion. By adjusting the composition of the film component and process parameters, permeability and barrier properties of the film may be fine-tuned. Inherently, the film has hydrophilic surfaces as well as hydrophilic pore surfaces. The microporous structure and the surface hydrophilicity of the film are more or less controlled by thermodynamics, thus to certain extent, it is a robust film formation process to make breathable films with hydrophilic surfaces. The inventive films can be recycled and reprocessed in the same way as traditional PE films. Such films would allow for EtO sterilization and global sale capability. The films meet a broad spectrum of packaging lines and products.

The surface of the film contains the PE-PEO graft copolymer, which provides surface hydrophilicity and biocompatibility. A non-woven structure so-formed has inherent desired tactile feel and compliance for skin-contact comfort. The grafted PEO brushes at the film surface can naturally serve as biofilm suppression agent, enabling effective healing and potential antibiotic treatment of infections if any. The end group of PEO can also be converted to diazeniumdialates, which is a nitric oxide releasing agent. This can add the nitric oxide controlled release functionality to the film, enabling continuous antimicrobial protection and wound healing promotion.

Various embodiments are listed below. It will be understood that the embodiments listed below may be combined not only as listed below, but in other suitable combinations in accordance with the scope of the disclosure.

A first aspect is a film for a medical device or packaging formed from a blend comprising: a base polymeric formulation comprising polyethylene and poly(ethylene oxide), the polyethylene being present in the blend in an amount in the range of about 50 to less than about 70% by weight and the poly(ethylene oxide) being present in the blend in an amount in the range of greater than about 25 to about 50% by weight; and an additive comprising a polyethylene-poly(ethylene oxide) amphiphilic graft copolymer (PE-g-PEO) being present in the blend in an amount in the range of about 0.01 to about 5.0% by weight; wherein the film is both breathable and a microbial barrier. The film may have an air permeability before sterilization in the range of about 3.5 to about 25 seconds per 100 cc according to Gurley Densometer Air Permeability Measurements and a percent permeation of less than 0.1%. The film may have a percent penetration in the range of about 0.001 to about 0.075%. The film may be in the form of wound dressing or medical device packaging.

The PE-g-PEO may be a product of ethylene oxide ring-opening polymerization of an ethylene vinyl acetate copolymer having from 10 to 40 weight percent of vinyl acetate, wherein the PE-g-PEO is according to Formula (I):

wherein R is hydrogen, alkyl, substituted alkyl, vinylic substituted alkyl, hydrocarbyl, substituted hydrocarbyl, or vinylic substituted hydrocarbyl group; the molar value of m is in the range from 2 to 40 mole percent; the molar value of n is in the range from 60 to 98 mole percent; and p is in the range from 5 to 500 ethylene oxide units.

The film of claim 1, wherein the PE-g-PEO has a molecular weight in the range of about 400 to about 500 kDa, a Brush Density in the range of 17-18, and an Average EO Units in Brush in the range of 120-125. The PE-g-PEO may comprise PVOH460-g-PEO7. A portion of the PEO of the amphiphilic graft copolymer (PE-g-PEO) may comprise end groups converted to a nitric oxide-releasing agent. The nitric oxide-releasing agent may comprise a diazeniumdiolate.

Another aspect is a microbial agent for inclusion in medical devices comprising: an olefin-poly(ethylene oxide)

amphiphilic graft copolymer, wherein a portion of the poly(ethylene oxide) comprises end groups converted to a nitric oxide-releasing agent. The nitric oxide-releasing agent comprises a diazeniumdiolate.

The amphiphilic graft copolymer may comprise a polyethylene-poly(ethylene oxide) amphiphilic graft copolymer (PE-g-PEO), a polypropylene-poly(ethylene oxide) amphiphilic graft copolymer (PP-g-PEO), or mixtures thereof.

In an embodiment, the amphiphilic graft copolymer comprises a polyethylene-poly(ethylene oxide) amphiphilic graft copolymer (PE-g-PEO) that is a product of ethylene oxide ring-opening polymerization of an ethylene vinyl acetate copolymer having from 10 to 40 weight percent of vinyl acetate wherein the PE-g-PEO is according to Formula (I):

(I)

wherein R is hydrogen, alkyl, substituted alkyl, vinylic substituted alkyl, hydrocarbyl, substituted hydrocarbyl, or vinylic substituted hydrocarbyl group; the molar value of m is in the range from 2 to 40 mole percent; the molar value of n is in the range from 60 to 98 mole percent; and p is in the range from 5 to 500 ethylene oxide units.

In an embodiment, the amphiphilic graft copolymer comprises a polypropylene-poly(ethylene oxide) amphiphilic graft copolymer (PP-g-PEO) that is a product of a polypropylene-maleic anhydride co-polymer (PP-MA) having from 10-50 weight percent of maleic anhydride wherein the PP-g-PEO is according to Formula (II):

(II)

wherein R is hydrogen, alkyl, substituted alkyl, vinylic substituted alkyl, hydrocarbyl, substituted hydrocarbyl, or vinylic substituted hydrocarbyl group; the molar percentages of grafted maleic anhydride units, m, is in the range from 2 to 10 mole percent; the molar values of propylene units, n, is in the range from 98 to 90 mole percent, and p is in the range of 5 to 500 ethylene oxide units.

An additional aspect is a wound dressing film comprising a blend of: a base polymeric formulation comprising polyethylene and poly(ethylene oxide); and any microbial agent disclosed herein; wherein the film is breathable and provides a microbial barrier. The nitric oxide-releasing agent may comprise a diazeniumdiolate. The wound dressing film may have an air permeability before sterilization in the range of about 3.5 to about 25 seconds per 100 cc according to Gurley Densometer Air Permeability Measurements and a percent permeation of less than 0.1%.

Another aspect is a method of making a medical device comprising: obtaining a polyethylene-poly(ethylene oxide) amphiphilic graft copolymer (PE-g-PEO); combining the PE-g-PEO with a base polymeric formulation comprising a polyethylene and a poly(ethylene oxide) to form a blend, which comprises: the polyethylene in an amount in the range of about 50 to less than about 70% by weight; the poly(ethylene oxide) in an amount in the range of greater than about 25 to about 50% by weight; and the PE-g-PEO in an amount in the range of about 0.01 to about 5.0% by weight; forming a film from the blend; wherein the film is both breathable and a microbial barrier. The film may have an air permeability before sterilization in the range of about 3.5 to about 25 seconds per 100 cc according to Gurley Densometer Air Permeability Measurements and a percent permeation of less than 0.1%.

The method may further comprise treating the film or the PE-g-PEO with a nitric oxide-releasing agent to convert end groups of a portion of the PEO. The nitric oxide-releasing agent may comprise a diazeniumdialate. The PE-g-PEO may be a product of ethylene oxide ring-opening polymerization of an ethylene vinyl acetate copolymer having from 10 to 40 weight percent of vinyl acetate, wherein the PE-g-PEO is according to Formula (I).

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

The following terms shall have, for the purposes of this application, the respective meanings set forth below.

Breathable films are those whose microporosities permit air permeability in such a way as to allow changes in atmospheric pressure (e.g., 0.5-10 psi) without breaking their seals. Breathable films are also suitable or ethylene oxide (EtO) sterilization. Breathable films may be tailored to have selective permeation rates to molecules of interest, for example, air/oxygen, carbon dioxide, and moisture. Many papers products are known to be highly breathable, that is, to permit high air permeability, but paper-based products are susceptible to difficulties in medical device packaging machines, and tearing and punctures during handling.

Films having microbial barriers exclude a desired percentage of a target challenge organism. Many papers are known to be ineffective microbial barriers due to their relatively large pore structure.

A base polymeric formulation is a material from which a film may be made. Preferably, the base polymeric formulations utilized in conjunction with the polyethylene-poly(ethylene oxide) amphiphilic graft copolymers (PE-g-PEOs) disclosed herein comprise polyethylene (PE) and poly(ethylene oxide) (PEO). An exemplary polyethylene includes but is not limited to linear low density polyethylene (LL-DPE). Exemplary PEOs have molecular weights of about 100 kg/mol. The base formulation may further include other ingredients, independently selected from one or more of the following: reinforcing and non-reinforcing fillers, plasticizers, antioxidants, stabilizers, processing oil, extender oils, lubricants, antiblocking, antistatic agents, waxes, foaming agents, pigments, flame retardants and other processing aids known in the compounding art. Fillers and extenders which can be utilized include conventional inorganics such as calcium carbonate, clays, silica, talc, titanium dioxide, carbon black, and the like. The processing oils generally are paraffinic, naphthenic or aromatic oils derived from petroleum fractions. The oils are selected from those ordinarily used in conjunction with the specific plastics or rubbers present in the formulation.

Reference to polyethylene-poly(ethylene oxide) amphiphilic graft copolymers (PE-g-PEO) means that a graft copolymer is formed from an ethylene-vinyl acetate containing monomer or prepolymer and poly(ethylene oxide), resulting in a polyethylene backbone and PEO side chains. The ethylene-vinyl acetate containing monomer or prepolymer may provide a desired functionality or reactivity to accept side chains, and they may have a polyethylene backbone with pendant groups suitable to incorporate PEO.

An additive is a component added to a formulation which is not reactive within the formulation.

Principles and embodiments of the present invention relate generally to films for a medical device or packaging made from a base polymeric formulation to which an additive comprising a polyethylene-poly(ethylene oxide) amphiphilic graft copolymer (PE-g-PEO) is added via melt process but can be incorporated via other mechanisms such dissolving in a compatible solvent. Methods of making and using these medical devices and components are also provided herein.

Embodiments of the present invention provide benefits over the prior art. The polyethylene-based films disclosed herein are breathable with microbial barrier properties. The films have a micro-porous structure and can provide excellent gas/liquid permeability, while maintaining a good barrier property. The major component of the film is polyethylene, which is hydrophobic while the surface of the film and porous structure itself is hydrophilic. Based on the materials used to make this film, the film will also have good biocompatibility. Upon treatment with a nitric-oxide releasing agent, the film will provide continuous antimicrobial protection and wound healing promotion.

PE-g-PEO graft copolymers have two kinds of segments. The PE segments are miscible with a polyolefin such as polyethylene, and the PEO segments are hydrophilic, which provides functionality at the surface of medical devices. Namely, the incorporation of polar, amorphous and flexible PEO segments in a crystalline hydrophobic polyolefin such as PE would lead to an increase in gas permeabilities, because PEO segments with polar ether oxygen units is known to have good affinity with $CO_2$, $H_2O$ molecules and with other light gases (e.g., He, $H_2$, $O_2$, $N_2$), thereby resulting in high level of sorption/solubility, diffusivity, and permeability.

General Procedure for Synthesis of PE-g-PEO & Preparation of Blend with Base Polymer Formulation Polyethylene-poly(ethylene oxide) amphiphilic graft copolymers (PE-g-PEO) are additives for the base polymeric formulations of components of medical devices. These copolymers are discussed in U.S. Pat. No. 9,150,674 to common assignee, which is incorporated herein by reference. The process to make amphiphilic graft copolymers involves grafting poly(ethylene oxide) onto an ethylene vinyl acetate (EVA) platform using oxo-anion ring-opening polymerization chemistry. Polyethylene based graft copolymers are prepared starting from poly(ethylene-co-vinyl acetate). The amphiphilic character will result from the incorporation of hydrophilic poly(ethyleneoxide) (PEO) side-chains.

A process for preparing amphiphilic polyethylene-based copolymers comprises obtaining an ethylene vinyl acetate copolymer having between 2-40 weight percent of vinyl acetate; reacting the ethylene vinyl acetate copolymer with potassium methoxide to prepare a mixture of polymeric potassium alkoxide and methyl acetate co-product; performing distillation on the a mixture of polymeric potassium alkoxide and methyl acetate co-product to remove the methyl acetate co-product; performing ethylene oxide ring-opening polymerization on the polymeric potassium alkoxide; removing aliquots during the ethylene oxide ring-opening polymerization to allow for systemic variation in degree of polymerization of ethylene oxide side chains; and collecting an amphiphilic polyethylene based graft co-polymer.

An exemplary PE-g-PEO copolymer is shown according to Formula (I).

Formula (I)

wherein R is hydrogen, alkyl, substituted alkyl, vinylic substituted alkyl, hydrocarbyl, substituted hydrocarbyl, or vinylic substituted hydrocarbyl group; the molar value of m is in the range from 2 to 40 mole percent; the molar value of n is in the range from 60 to 98 mole percent; and p is in the range from 5 to 500 ethylene oxide units. Reference to "n" is with respect to ethylene units, "m" is to grafted PEO units, and "p" is to ethylene oxide units of the grafted chain.

The molar percentage value of m may be in the range of from 10 to 40 mole percent. The molar percentage value of n may be in the range of from 60 to 90 mole percent. The molar percentage value of p may be in the range of from 5 to 400.

In one or more embodiments, the ethylene vinyl acetate copolymer has a melt index from 0.3 to 500 dg/min.

In one or more embodiments, the ethylene oxide ring-opening polymerization is performed at a reaction temperature in the range of −20 to 100° C. In a specific embodiment, the ethylene oxide ring-opening polymerization is performed at a reaction temperature of greater than 30° C. In another specific embodiment, the ethylene oxide ring-opening polymerization is performed at a reaction temperature of 60° C.

The ethylene oxide ring-opening polymerization may be performed under alkaline conditions. The ethylene oxide ring-opening polymerization may be performed using 1,3 propane sultone and/or triethylamine.

In one or more embodiments, the amphiphilic polyethylene based graft co-polymer has a dispersity index in the range of 2 to 10, or even 1.05 to 1.25.

An exemplary PE-g-PEO copolymer composition is listed in Table 1.

TABLE 1

Table 1. Exemplary PE-g-PEO copolymer

| Nomenclature (PE-XXX-g-PEO-z) | Molecular Weight (kDa) | Average —CH$_2$—CH$_2$— Interval Numbers (Brush Density) (n) | Average EO Units in Brush (p) | Mass Gain (%) |
|---|---|---|---|---|
| PE-460-g-PEO-7 | 447.6 | 17.4 | 122 | 1100 |

Combination of the polyethylene-poly(ethylene oxide) amphiphilic graft copolymer (PE-g-PEO) with the base polymeric formulation is done via melt processing. The term "melt processing" is used to mean any process in which polymers, such as the polyolefin, are melted or softened. Melt processing includes extrusion, pelletization, film blowing or casting, thermoforming, compounding in polymer melt form, fiber spinning, or other melt processes.

Any equipment suitable for a melt processing can be used as long as it provides sufficient mixing and temperature control. For instance, a continuous polymer processing system such as an extruder, a static polymer mixing device such as a Brabender blender, or a semi-continuous polymer processing system, such as a BANBURY mixer, can be used. The term "extruder" includes any machine for polyolefin extrusion. For instance, the term includes machines that can extrude material in the form of powder or pellets, sheets, fibers, or other desired shapes and/or profiles. Generally, an extruder operates by feeding material through the feed throat (an opening near the rear of the barrel) which comes into contact with one or more screws. The rotating screw(s) forces the polyolefin forward into one or more heated barrels (e.g., there may be one screw per barrel). In many processes, a heating profile can be set for the barrel in which three or more independent proportional-integral-derivative controller (PID)-controlled heater zones can gradually increase the temperature of the barrel from the rear (where the plastic enters) to the front. When a melt extrusion is used, the mixing can take place during the melt extrusion step. The heat produced during the extrusion step provides the energy necessary for the mixing between different components. A temperature at or above the melting temperature of the polymer may be maintained for a time sufficient to mix all the components. For instance, the mixing time may be at least 5 seconds, at least 10 seconds, or at least 15 seconds. Typically, the mixing time is 15-90 seconds.

Suitable blending temperature during melt mixing of polyethylene, PEO, and the additive should be sufficient to melt or to soften the component of the composition which has the highest melting or softening point. The temperature typically ranges from 60 to 300° C., for instance, from 100 to 280° C., from 90 to 150° C. One skilled in the art understands that a polyolefin typically melts or softs over a temperature range rather than sharply at one temperature. Thus, it may be sufficient that the polyolefin be in a partially molten state. The melting or softening temperature ranges can be approximated from the differential scanning calorimeter (DSC) curve of the polyolefin.

The three components, PE, PEO, and PE-g-PEO, are metered into a twin screw extruder. The feeding can be done through three individual feeders or one or two feeders by combining the components accordingly. A homogeneous blend is achieved after mixed in the twin-screw extruder at elevated temperature.

Table 2. Exemplary Formulations (with the Proviso that the Ingredients Total 100 wt. %).

TABLE 2

| Blend Ingredient | A by weight | B by weight |
|---|---|---|
| Base Polymeric Formulation | 95-99.99% | 95-99.99% |
| Polyethylene | 50-<70% | 55-65% |
| Poly(ethylene oxide) | >25-50% | 30-45% |
| Optional further ingredients | 0-10% | 0-10% |
| Polyethylene-poly(ethylene oxide) amphiphilic graft copolymer (PE-g-PEO) additive | 0.01-5% | 0.01-5% |

In one or more embodiments, including Exemplary Formulations A and B, and C, the polyethylene-poly(ethylene oxide) amphiphilic graft copolymer (PE-g-PEO) additive may be present in amounts of 0.01 to about 5.0% by weight; about 0.1 to about 4.0% by weight; about 0.2 to about 2.5% by weight; about 0.25 to about 1% by weight; or about 0.5 weight %. In one or more embodiments, including Exemplary Formulations A and B, and C, the poly(ethylene oxide) may be present in amounts of greater than 25 to about 50% by weight, or about 25.1 to about 50% by weight; about 30 to about 45% by weight; about 35 to about 43% by weight; or even about 40% by weight. In one or more embodiments, including Exemplary Formulations A and B, and C, the polyethylene may be present in amounts of 50 to less than 70% by weight, or about 50 to about 69.9% by weight; about 53 to about 65% by weight; about 55 to about 65% by weight; or even about 55-59.5% by weight.

Suitable linear low density polyethylene (LLDPE) for use in the process of the invention include copolymers of ethylene and α-olefins. Alpha-olefins include 1-butene, 1-hexene, and 1-octene, the like, and mixtures thereof. The density of LLDPE is preferably within the range of about 0.865 to about 0.925 g/cm$^3$ (ASTM D792-13) and a melt mass flow rate of less than 0.5 g/10 min to greater than 20 g/10 min based on the requirements of the manufacturing process and end application (190° C./2.16 kg, ASTM D1238-13). LLDPE is commercially available, for instance Dowlex™ 2045.01 G LLDPE from Dow Chemical Company. Suitable LLDPE can be produced by a Ziegler, single-site, or any other olefin polymerization catalysts.

Suitable commercially available poly(ethylene oxides) (PEO) have molecular weights in the range of 5,000 and 200,000 g/mol. For example, PEO 5 kDa, PEO 100 kDA, and PEO 200 kDA. PEOs of varying molecular weights may be used in combination. PEO resins may have a solubility in water of from 0.1% to 100% at 20° C. and atmospheric pressure.

General Procedure for Synthesis of PP-g-PEO

Polypropylene-poly(ethylene oxide) amphiphilic graft copolymers (PP-g-PEO) are discussed in U.S. Pat. No. 9,150,674 to common assignee, which is incorporated herein by reference. The process to make amphiphilic graft copolymers involves grafting poly(ethylene oxide) onto maleated polypropylene platform using oxo-anion ring-opening polymerization chemistry. Polypropylene based graft copolymers are prepared starting from maleic anhydride grafted isotactic polypropylene. The amphiphilic character will result from the incorporation of hydrophilic poly(ethylene-oxide) (PEO) side-chains.

Preparation of amphiphilic polypropylene-based copolymers comprise: obtaining a maleic anhydride grafted polypropylene wherein the molar percentages of grafted maleic anhydride units is in the range from 2 and 10 mole percent; the molar values of propylene units is in the range from 98 to 90 mole percent; reacting the maleic anhydride grafted polypropylene with a reducing agent to prepare a iPP-diol copolymer, wherein the diol content is equal to the molar percentage of the originally grafted maleic anhydride units:

and subsequently performing ethylene oxide ring-opening polymerization on the iPP-diol copolymer; and isolating an amphiphilic iPP-g-PEO copolymer.

An exemplary PP-g-PEO copolymer is shown according to Formula (II).

Formula (II)

wherein R represents the end-groups present in either Ziegler-Natta or metallocene catalyzed polypropylene including, but not limited to, hydrogen, alkyl, substituted alkyl, vinylic substituted alkyl, hydrocarbyl, substituted hydrocarbyl, or vinylic substituted hydrocarbyl group; the molar percentages of grafted maleic anhydride units, m, is in the range from 2 to 10 mole percent; the molar values of propylene units, n, is in the range from 98 to 90 mole percent; and p is in the range of 5 to 500. The amount of diol after reduction of the maleic anhydride may be in the range from 2 to 10 mole percent.

The molar percentage value of propylene may be in the range of from 90 to 98 mole percent, the molar percentage value of diol derived from reduction of maleic anhydride may be in the range of from 10 to 2 mole percent, and the molar percentage value of p may be in the range of from 5 to 400 mole percent.

In one or more embodiments, the ethylene oxide ring-opening polymerization is performed at a reaction temperature in the range of −20 to 150° C. In a specific embodiment, the ethylene oxide ring-opening polymerization is performed at a reaction temperature of greater than 30° C. In another specific embodiment, the ethylene oxide ring-opening polymerization is performed at a reaction temperature of 130° C.

The ethylene oxide ring-opening polymerization may performed under alkaline conditions. The ethylene oxide ring-opening polymerization may be performed using 1,3 propane sultone and/or triethylamine.

In one or more embodiments, the amphiphilic iPP-g-PEO copolymer has a dispersity index in the range of 2 to 8.

General Procedure for Formation of Medical Devices and/or Packaging

Base polymeric materials with PE-g-PEO additive prepared with according to the process of the invention may be formed into useful articles by standard forming methods known in the art, e.g., by blown film extrusion, cast film extrusion, injection or blow molding, pelletizing, foaming, thermoforming, compounding in polymer melt form, or fiber spinning. For example, any technique discussed above in the embodiments describing the melt processes can be used to prepare modified polymer, thereby forming various useful articles, depending on the type of melt processing technique used.

With regard to films, the blends herein may generally be used to form desired films, such as blown or cast films. The techniques of blown film extrusion and cast film are known to one skilled in the art in the area of production of thin plastic films.

Polymers with PE-g-PEO additive may also be used in coextruded films. The formation of coextruded blown films is known to one skilled in the art. The term "coextrusion" refers to the process of extruding two or more materials through a single die with two or more orifices arranged such that the extrudates merged together into a laminar structure, for instance, before chilling or quenching. If a cast film die is attached to the twin-screw extruder, a cast film can be formed at the end of the blending process. Otherwise, the blend is pelletized into pellets and can be run through a blown-film process for forming. The film runs through a water or solvent bath to remove the PEO component, either online or offline.

Typically the film formation process for polyethylene is through blow filming. To make it a breathable microbial barrier film suitable for medical applications, a non-woven fabrication process is typically adopted to control the microstructure of the film. The film may be manufactured through a combination of melt blending, film forming, and extraction process. It may be a combination of distinct unit operations or a continuous process. Either way, polyethylene (PE) is melted blended with poly(ethylene oxide) (PEO) and polyethylene-grafted-poly(ethylene oxide) (PE-g-PEO). The composition of the blends is controlled to achieve a desired microstructure. The blends then go through a film forming process to form a film with thickness range from 1 μm to tens of μm. The film is extracted with water or other solvent to wash away one of the blend component, PEO, to form micro-porous structure.

Applications

Films disclosed herein can provide combined functionalities of hydrocolloids dressing and foam dressing: good moisture permeability, microbial barrier properties, fluid/liquid discharge functionalities, and the option to have a controlled-release antimicrobial/healing promotion agent. It does not require a backing material. It can also serve as the functional film for negative pressure wound therapy.

Films disclosed herein may be used for wound dressing. The hydrophilic surface is biocompatible and can provide a comfortable skin contact. The gas permeability makes the wound dressing breathable and helps the healing process. The barrier property can prevent any further infection. The liquid permeability provides the option for fluid discharge from wound if any to pass through the dressing and prevents the possibility of pressure building up inside the dressing. The film could also be used for filtration application. The hydrophilic surface works excellent for, but not limited to, aqueous solutions. The great biocompatibility of the film makes it suitable for bio-filtration purpose as well, for example blood filtration, and etc. The hydrophilic surface property and the good permeability make the film suitable for any skin-contact patch kind of applications. It can also be used for a diaper liner.

The films disclosed herein provide a unique combination of properties and functions that can satisfy all the requirements for wound dressing. The major construction of the film is polyethylene, which provides excellent mechanical performance and integrity. This can serve as the carrier function of the dressing. The film also has excellent permeability, which can transport any discharge from wound to outside to minimize any inside pressure buildup. In addition, the film can transport air or moisture to the wound to promoting healing. The barrier property of the film can prevent the wound from further contaminating with bacteria or any other forms of external infection. The surface of the film and the surface of its porous structure are hydrophilic, which renders them biocompatible and suitable for skin/wound contact. The surface of the film and the surface of its porous structure are covered with polyethylene oxide. The PEO chains at the surface can serve two functions. First, the PEO chains at the surface can form a brush layer and prevent any biofilm formation. Second, the PEO chains can also adjust the moisture environment of the wound which can promote the healing process.

Films disclosed herein may also be used for packaging applications where there are requirements of gas permeability like ethylene oxide (EtO) sterilization and barrier properties. Polymer films for medical device packaging are subjected to a broad range of stringent criteria which includes: providing a sterile barrier and structural support for the product over the life of the product (up to 5 years) post-sterilization; capable of high fabrication rates with a broad fabrication window; cost effective; meeting demands/limitations of expanding, global market; meeting increasing demands for environmental stewardship.

Embodiments

Various embodiments are listed below. It will be understood that the embodiments listed below may be combined with all aspects and other embodiments in accordance with the scope of the invention.

Embodiment 1

A film for a medical device or packaging formed from a blend comprising: a base polymeric formulation comprising polyethylene and poly(ethylene oxide), the polyethylene being present in the blend in an amount in the range of about 50 to less than about 70% by weight and the poly(ethylene oxide) being present in the blend in an amount in the range of greater than about 25 to about 50% by weight; and an additive comprising a polyethylene-poly(ethylene oxide) amphiphilic graft copolymer (PE-g-PEO) being present in the blend in an amount in the range of about 0.01 to about 5.0% by weight; wherein the film is both breathable and a microbial barrier.

Embodiment 2

The film of embodiment 1, wherein the film has an air permeability before sterilization in the range of about 3.5 to about 25 seconds per 100 cc according to Gurley Densometer Air Permeability Measurements and a percent permeation of less than 0.1%.

Embodiment 3

The film of embodiment 2 having a percent penetration in the range of about 0.001 to about 0.075%.

Embodiment 4

The film of one of embodiments 1 to 3 in the form of wound dressing or medical device packaging.

Embodiment 5

The film of one of embodiments 1 to 4, wherein the PE-g-PEO is a product of ethylene oxide ring-opening polymerization of an ethylene vinyl acetate copolymer having from 10 to 40 weight percent of vinyl acetate, wherein the PE-g-PEO is according to Formula (I):

wherein R is hydrogen, alkyl, substituted alkyl, vinylic substituted alkyl, hydrocarbyl, substituted hydrocarbyl, or vinylic substituted hydrocarbyl group; the molar value of m is in the range from 2 to 40 mole percent; the molar value of n is in the range from 60 to 98 mole percent; and p is in the range from 5 to 500 ethylene oxide units.

Embodiment 6

The film of one of embodiments 1 to 5, wherein the PE-g-PEO has a molecular weight in the range of about 400 to about 500 kDa, a Brush Density in the range of 17-18, and an Average EO Units in Brush in the range of 120-125.

Embodiment 7

The film of one of embodiments 1 to 6, wherein the PE-g-PEO comprises PVOH460-g-PEO7.

Embodiment 8

The film of one of embodiments 1 to 7, wherein a portion of the PEO of the amphiphilic graft copolymer (PE-g-PEO) comprises end groups converted to a nitric oxide-releasing agent.

Embodiment 9

The film of embodiment 8, wherein the nitric oxide-releasing agent comprises a diazeniumdiolate.

Embodiment 10

A microbial agent for inclusion in medical devices comprising: an olefin-poly(ethylene oxide) amphiphilic graft copolymer, wherein a portion of the poly(ethylene oxide) comprises end groups converted to a nitric oxide-releasing agent.

Embodiment 11

The microbial agent of embodiment 10, wherein the nitric oxide-releasing agent comprises a diazeniumdiolate.

Embodiment 12

The microbial agent of one of embodiments 10 to 11, wherein the amphiphilic graft copolymer comprises a poly-ethylene-poly(ethylene oxide) amphiphilic graft copolymer (PE-g-PEO), a polypropylene-poly(ethylene oxide) amphiphilic graft copolymer (PP-g-PEO), or mixtures thereof.

Embodiment 13

The microbial agent of one of embodiments 10 to 12, wherein the amphiphilic graft copolymer comprises a poly-ethylene-poly(ethylene oxide) amphiphilic graft copolymer (PE-g-PEO) that is a product of ethylene oxide ring-opening polymerization of an ethylene vinyl acetate copolymer having from 10 to 40 weight percent of vinyl acetate wherein the PE-g-PEO is according to Formula (I):

(I)

wherein R is hydrogen, alkyl, substituted alkyl, vinylic substituted alkyl, hydrocarbyl, substituted hydrocarbyl, or vinylic substituted hydrocarbyl group; the molar value of m is in the range from 2 to 40 mole percent; the molar value of n is in the range from 60 to 98 mole percent; and p is in the range from 5 to 500 ethylene oxide units.

Embodiment 14

The microbial agent of one of embodiments 10 to 12, wherein the amphiphilic graft copolymer comprises a poly-propylene-poly(ethylene oxide) amphiphilic graft copolymer (PP-g-PEO) that is a product of a polypropylene-maleic anhydride co-polymer (PP-MA) having from 10-50 weight percent of maleic anhydride wherein the PP-g-PEO is according to Formula (II):

(II)

wherein R is hydrogen, alkyl, substituted alkyl, vinylic substituted alkyl, hydrocarbyl, substituted hydrocarbyl, or vinylic substituted hydrocarbyl group; the molar percentages of grafted maleic anhydride units, m, is in the range from 2 to 10 mole percent; the molar values of propylene units, n, is in the range from 98 to 90 mole percent, and p is in the range of 5 to 500 ethylene oxide units.

Embodiment 15

A wound dressing film comprising a blend of: a base polymeric formulation comprising polyethylene and poly(ethylene oxide); and the microbial agent of one of embodiments 10 to 14; wherein the film is breathable and provides a microbial barrier.

Embodiment 16

The wound dressing film of embodiment 15, wherein the nitric oxide-releasing agent comprises a diazeniumdiolate.

Embodiment 17

The wound dressing film of embodiment 15 having an air permeability before sterilization in the range of about 3.5 to about 25 seconds per 100 cc according to Gurley Densometer Air Permeability Measurements and a percent permeation of less than 0.1%.

Embodiment 18

A method of making a medical device comprising: obtaining a polyethylene-poly(ethylene oxide) amphiphilic graft copolymer (PE-g-PEO); combining the PE-g-PEO with a base polymeric formulation comprising a polyethylene and a poly(ethylene oxide) to form a blend, which comprises: the polyethylene in an amount in the range of about 50 to less than about 70% by weight; the poly(ethylene oxide) in an amount in the range of greater than about 25 to about 50% by weight; and the PE-g-PEO in an amount in the range of about 0.01 to about 5.0% by weight; forming a film from the blend; wherein the film is both breathable and a microbial barrier.

Embodiment 19

The method of embodiment 18 wherein the film has an air permeability before sterilization in the range of about 3.5 to about 25 seconds per 100 cc according to Gurley Densometer Air Permeability Measurements and a percent permeation of less than 0.1%.

Embodiment 20

The method of embodiment 18 or 19 further comprising treating the film or the PE-g-PEO with a nitric oxide-releasing agent to convert end groups of a portion of the PEO.

Embodiment 21

The method of embodiment 20, wherein the nitric oxide-releasing agent comprises a diazeniumdialate.

Embodiment 22

The method of any one of embodiments 18 to 21, wherein the PE-g-PEO is a product of ethylene oxide ring-opening polymerization of an ethylene vinyl acetate copolymer having from 10 to 40 weight percent of vinyl acetate, wherein the PE-g-PEO is according to Formula (I):

(I)

wherein R is hydrogen, alkyl, substituted alkyl, vinylic substituted alkyl, hydrocarbyl, substituted hydrocarbyl, or vinylic substituted hydrocarbyl group; the molar value of m is in the range from 2 to 40 mole percent; the molar value of n is in the range from 60 to 98 mole percent; and p is in the range from 5 to 500 ethylene oxide units.

EXAMPLES

The PE-g-PEO graft copolymer tested herein was prepared according to the methods of U.S. Pat. No. 9,150,674. Specifically, polyethylene based graft copolymer was prepared from a poly(ethylene-co-vinyl acetate) starting material. Controlled ring-opening polymerization is used to graft polymer side chains of ethylene oxide onto the polyethylene backbone to prepare polyethylene-graft-poly(ethylene oxide) (PE-g-PEO) copolymers having functionalized side groups. Incorporation of hydrophilic poly(ethylene oxide) (PEO) side-chains onto the polyethylene backbone resulted a copolymer with desired amphiphilic characteristics.

More specifically, the amphiphilic graft copolymer of the present invention was prepared in a two-step synthetic sequence. First, a hydrolysis reaction was performed on the EVA platform whereby the acetate units were removed to produce ethylene vinyl alcohol copolymers (EVOH) and a methyl acetate co-product. The acetate units were removed by reaction with potassium methoxide and the co-product methyl acetate will be removed by distillation. The resultant polymeric potassium alkoxide was then used to initiate ethylene oxide ring-opening polymerization (ROP). In the second step of the process, oxo-anion polymerization was performed on the copolymer of ethylene and vinyl acetate to produce the novel polyethylene based graft-copolymer.

The PE-g-PEO prepared and used in Examples 1-3 was PE-460-g-PEO-7, having a molecular weight of 447.6 kDa, an Average —$CH_2$—$CH_2$— Interval Numbers (Brush Density)(n) of 17.4, an Average EO Units in Brush (p) of 122, and a Mass Gain (%) of 1100.

Example 1

A series of melt blends was made. The following components were dry mixed: a linear low density polyethylene (LLDPE) Dowlex™ 2045, poly(ethylene oxide) (PEO) (100 kg/mol), and the PE-460-g-PEO-7. In a twin-screw blender (Brabender Model R.E.E. 6) having a rotor speed of 20 rpm at 150-160° C., the LLDPE, PE-460-g-PEO-7, and PEO were fed in sequence. The rotor speed was increased to 150 rpm upon the melt of all feeding materials. The temperature was kept at 150-160° C. for 5 minutes. Upon completion of batch mixing, the blend was rapidly quenched in liquid nitrogen to freeze the morphology.

Example 2

A series of films having the following composition were formed.

| Blend Ingredient | Example 2 by weight |
|---|---|
| Polyethylene | 55% |
| Poly(ethylene oxide) | 40% |
| Polyethylene-poly(ethylene oxide) amphiphilic graft copolymer (PE-g-PEO) additive | 5% |

Films were made as follows. A blend prepared according to Example 1 was cut to small pieces, which were placed between sheets of Kapton films and then placed between the heated metal platens of a compression press (Carver, Inc). The thickness of films was controlled with 0.08 mm aluminum foil at 150-155° C. and 15,000 PSI for 60 seconds. The films were quenched in liquid nitrogen once left the hot plates. The films of polymer blends were pealed in liquid nitrogen.

Summary of the films.

| | Film x counts[1] | | |
|---|---|---|---|
| | Example 2-A × 4 | Example 2-B × 2 | Example 2-C × 3 |
| Temperature (° C.) | 150 | 150 | 150 |
| Pressure (PSI) | 15,000 | 15,000 | 15,000 |
| Molding Plates | Kapton | Kapton | Kapton |
| Template Size (cm$^2$) | 36 | 36 | ~100 |
| Template Thickness (mm) | 0.08 | 0.16 | 0.24 |
| Surfactant | None | None | None |
| Peeling Method | −196° C. | −196° C. | −196° C. |

[1]"x counts" refers to film layer counts.

Porous films were obtained from the pressed blends, followed by PEO extraction with water at room temperature for 24 hours. Then the films were dried at room temperature under a high vacuum.

The Aerosol Challenge Test used *Bacillus atrophaeus* as the challenge organism. Percent penetration was calculated from the microbial challenge for each sample. The pressure differential was 2"Hg.

The Gurley Densometer Air Permeability Measurements were obtained based on time required in seconds for 100 cc of air to pass through material at a constant pressure per square inch of material.

Summary of film properties, gas permeability and antimicrobial barrier, versus reference materials.

| Material | Permeable Material Aerosol Challenge Test | | Gurley Densometer Air Permeability |
|---|---|---|---|
| | Air Flow Rate (LPM) | % Penetration | Measurements (seconds per 100 cc) No sterilization |
| PE/PEO/PE-g-PEO films of Examples 2-A, 2-B, 2-C | 4.2-6.4 | 0.017-0.071 | 3.5-7.7 |
| Reference material Breathable paper | 0.26 | 0.004 | 211.6 |
| Reference material 0.85 μm filter | 6.1 | 0.001 | 5.4 |

The PE/PEO/PE-g-PEO films provide both acceptable gas permeability (breathability) and antimicrobial barrier properties. Surface FTIR results show a PEO peak.

Figure 1:
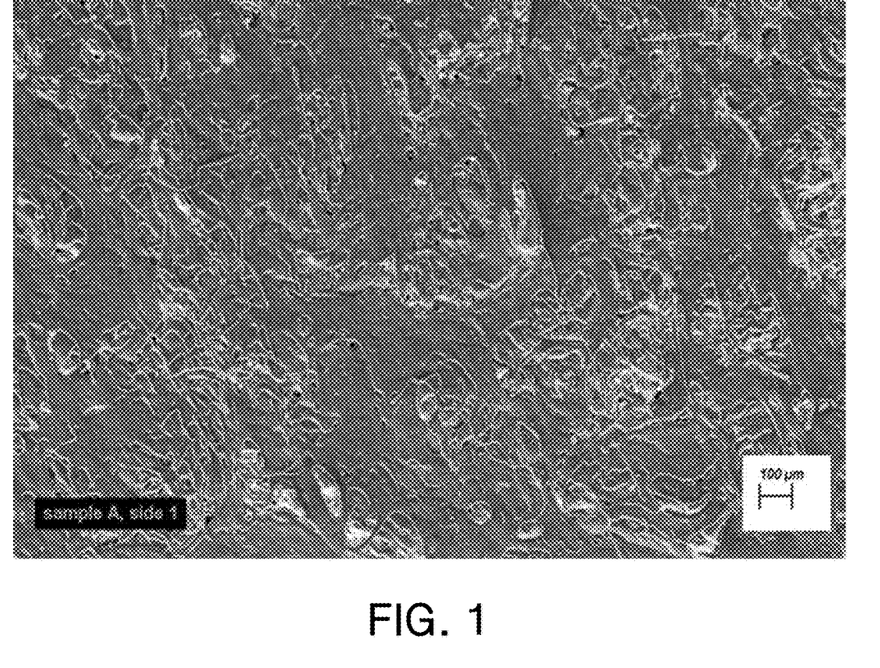
FIG. 1 provides a Scanning Electron Microscope (SEM) micrograph of the surface of a film according to an embodiment.

FIG. 1 is a Scanning Electron Microscope (SEM) micrograph of the surface of the film according to Example 2-A at a magnification of 100× on a scale of 100 μm (Signal A=SE2, Aperture Size 30.00 μm, EHT=10.00 kV, WD=11.0 mm, Probe=200.0 nA).

Figure 2:
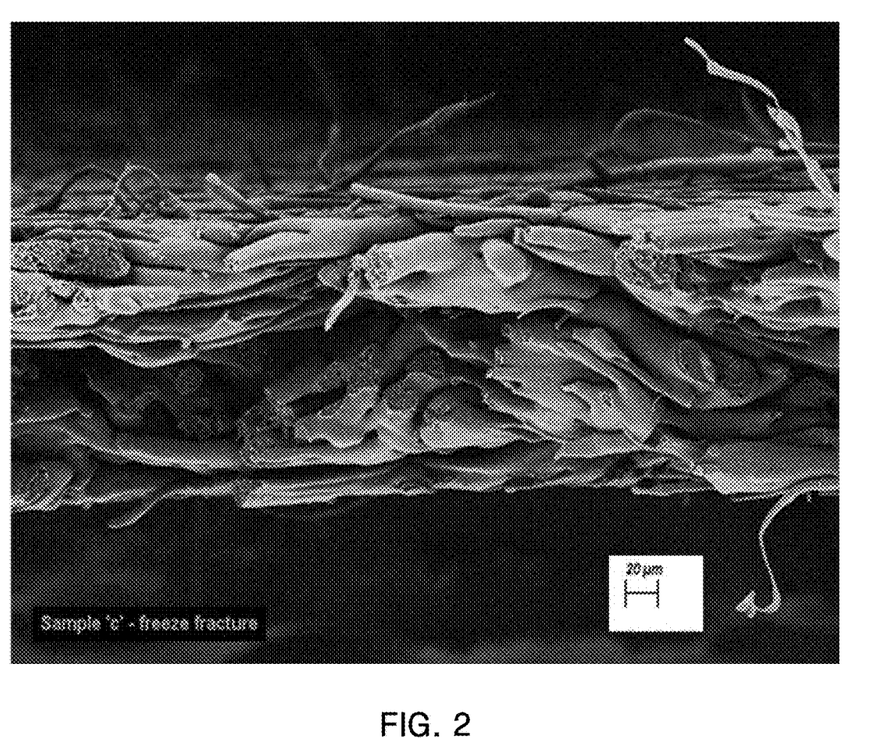
FIG. 2 provides a Scanning Electron Microscope (SEM) micrograph of the cross-section of a film according to an embodiment.

FIG. 2 is a Scanning Electron Microscope (SEM) micrograph of the cross-section of the film according to Example 2-C at a magnification of 500× on a scale of 20 μm (Signal A=QBSA, Aperture Size 30.00 μm, EHT=10.00 kV, WD=10.4 mm, Probe=200.0 nA).

Figure 3:
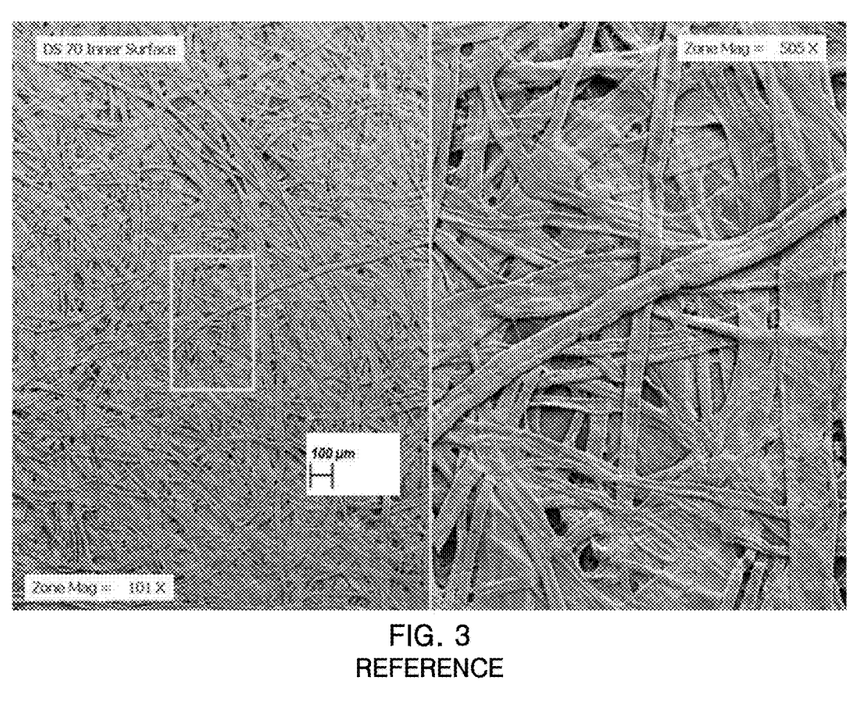
FIG. 3 provides Scanning Electron Microscope (SEM) micrographs of the surface of a breathable paper reference material at two magnifications.

FIG. 3 provides Scanning Electron Microscope (SEM) micrographs at two magnifications (100× and 500×) of the surface of a breathable paper reference material (Signal A=SE2, Aperture Size 30.00 μm, EHT=5.00 kV, WD=9.8 mm, Vacuum mode=high vacuum).

Mechanical properties of an inventive film, reference material, and comparative PE film are provided.

| | Tensile Strength (PSI) | Elongation at break | Puncture (lbf) | Tear (gram) |
|---|---|---|---|---|
| PE/PEO/PE-g-PEO film of Example 2 | 389 | 50% | 1.7 | 88 |
| Reference material Breathable paper | 7243 | 6% | 4.7 | 47 |
| PE Film Comparative | 25800 | 500% | 4.7 | 310 |

Example 3

A series of films with varying compositions as follows were formed.

| Blend Ingredient | Example 3-A by weight | Example 3-B by weight | Example 3-C by weight | Example 3-D by weight |
|---|---|---|---|---|
| Polyethylene | 59.5% | 59.0% | 57.5% | 57.5% |
| Poly(ethylene oxide) | 40.0% | 40.0% | 40.0% | 40.0% |
| Polyethylene-poly(ethylene oxide) amphiphilic graft copolymer (PE-g-PEO) additive | 0.5% | 1.0 | 2.5 | 2.5 |

Films were made according to Example 2.

Summary of the films.

| Film x counts[1] | Example 3-A × 1 | Example 3-B × 1 | Example 3-C × 3 | Example 3-D × 1 |
|---|---|---|---|---|
| Temperature (° C.) | 150 | 150 | 150 | 150 |
| Pressure (PSI) | 15,000 | 15,000 | 15,000 | 15,000 |
| Molding Plates | Aluminum Foil | Aluminum Foil | Aluminum Foil | Aluminum Foil |
| Template Size (cm$^2$) | 36 | 36 | 36 | 100 |
| Template Thickness (mm) | 0.2 | 0.2 | 0.2 | 0.2 |
| Surfactant | None | None | None | None |
| Peeling Method | Liquid N$_2$ | Liquid N$_2$ | Liquid N$_2$ | Liquid N$_2$ |

[1]x counts refers to film layer counts.

Porous films were obtained from the pressed blends, followed by PEO extraction with water at room temperature for 24 hours. Then the films were dried at room temperature under a high vacuum.

Summary of film properties, gas permeability and antimicrobial barrier, versus a reference material tested as set forth in Example 2.

| Material | Permeable Material Aerosol Challenge Test | | Gurley Densometer Air Permeability |
|---|---|---|---|
| | Air Flow Rate (LPM) | % Penetration | Measurements (seconds per 100 cc) No sterilization |
| PE/PEO/PE-g-PEO film of Example 3-A | 2.00 | 0.044 | 5.4 |
| PE/PEO/PE-g-PEO film of Example 3-B | 0.82 | 0.013 | 23.8 |
| PE/PEO/PE-g-PEO film of Example 3-C | 1.05 | 0.004 | 24.3 |
| PE/PEO/PE-g-PEO film of Example 3-D | 1.65 | 0.005 | 17.3 |
| Reference material Breathable paper | 0.24 | 0.006 | 157.0 |

The PE/PEO/PE-g-PEO films provide both acceptable gas permeability (breathability) and antimicrobial barrier properties.

Contact angle measurements were also performed on the films. The surfaces of the films can be completely wetted. The water drop instantly absorbed into the porous structure instantly and completely wetted the pore surface as well. This demonstrated that both the surface of the film and the surface of the porous structure are hydrophilic.

The PE/PEO/PE-g-PEO single or multilayer films are easily processed on conventional cast and blown film lines within standard polyolefin operating parameters and can be reprocessed easily.

Example 4

Inventive films according to Examples 2-3 are treated to convert a portion of end groups of the PEO of the polyethylene-poly(ethylene oxide) amphiphilic graft copolymer (PE-g-PEO) to include a nitric oxide-releasing agent. The treatment is according to the following reactions.

PE-PEO-OH---->(PE-PEO-SH)----->PE-PEO-diazeniumdiolates (nitric oxide releasing agent).

Example 5

An olefin-poly(ethylene oxide) amphiphilic graft copolymer is reacted with a precursor of a nitric oxide-releasing agent to form a microbial additive that may be used as an ingredient in a base polymeric formulation for forming medical devices. One such copolymer is polyethylene-poly(ethylene oxide) amphiphilic graft copolymer (PE-g-PEO), which is prepared according to the methods of U.S. Pat. No. 9,150,674. Another such copolymer is polypropylene-poly(ethylene oxide) amphiphilic graft copolymer (PP-g-PEO), which is prepared according to the methods of U.S. Pat. No. 9,150,674. The reaction is according to the following.

PE-PEO-OH---->(PE-PEO-SH)----->PE-PEO-diazeniumdiolates (nitric oxide releasing agent); or PP-PEO-OH---->(PP-PEO-SH)----->PP-PEO-diazeniumdiolates (nitric oxide releasing agent).

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A film for a medical device or packaging formed from a blend comprising:
   a base polymeric formulation comprising polyethylene and poly(ethylene oxide), the polyethylene being present in the blend in an amount in the range of about 50 to less than 70% by weight and the poly(ethylene oxide) being present in the blend in an amount in the range of greater than 25 to about 50% by weight; and
   an additive comprising a polyethylene-poly(ethylene oxide) amphiphilic graft copolymer (PE-g-PEO) being present in the blend in an amount in the range of about 0.01 to about 5.0% by weight, wherein a portion of the PEO of the amphiphilic graft copolymer (PE-g-PEO) comprises end groups directly bonded to a nitric oxide-releasing agent;
   wherein the film is both breathable and a microbial barrier.

2. The film of claim 1, wherein the film has an air permeability before sterilization in the range of about 3.5 to about 25 seconds per 100 cc according to Gurley Densometer Air Permeability Measurements and a percent permeation of less than 0.1%.

3. The film of claim 2 having a percent penetration in the range of about 0.001 to about 0.075%.

4. The film of claim 1 in the form of wound dressing or medical device packaging.

5. The film of claim 1, wherein the PE-g-PEO is a product of ethylene oxide ring-opening polymerization of an ethylene vinyl acetate copolymer having from 10 to 40 weight percent of vinyl acetate, wherein the PE-g-PEO is according to Formula (I):

(I)

wherein R is hydrogen, alkyl, substituted alkyl, vinylic substituted alkyl, hydrocarbyl, substituted hydrocarbyl, or vinylic substituted hydrocarbyl group; the molar value of m is in the range from 2 to 40 mole percent; the molar value of n is in the range from 60 to 98 mole percent; and p is in the range from 5 to 500 ethylene oxide units.

6. The film of claim 1, wherein the PE-g-PEO has a molecular weight in the range of about 400 to about 500 kDa, a Brush Density in the range of 17-18, and an Average EO Units in Brush in the range of 120-125.

7. The film of claim 6, wherein the PE-g-PEO comprises PVOH460-g-PEO7.

8. The film of claim 1, wherein the nitric oxide-releasing agent comprises a diazeniumdiolate.

9. A wound dressing film comprising a blend of:
   a base polymeric formulation comprising polyethylene and poly(ethylene oxide); and
   a microbial agent comprising: an olefin-poly(ethylene oxide) amphiphilic graft copolymer, wherein a portion of the poly(ethylene oxide) comprises end groups converted to a nitric oxide-releasing agent;
   wherein the film is breathable and provides a microbial barrier.

10. The wound dressing film of claim 9, wherein the nitric oxide-releasing agent comprises a diazeniumdiolate.

11. The wound dressing film of claim 9 having an air permeability before sterilization in the range of about 3.5 to about 25 seconds per 100 cc according to Gurley Densometer Air Permeability Measurements and a percent permeation of less than 0.1%.

12. The wound dressing film of claim 9, wherein the amphiphilic graft copolymer comprises a polyethylene-poly(ethylene oxide) amphiphilic graft copolymer (PE-g-PEO), a polypropylene-poly(ethylene oxide) amphiphilic graft copolymer (PP-g-PEO), or mixtures thereof.

13. The wound dressing film of claim 9, wherein the amphiphilic graft copolymer comprises a polyethylene-poly(ethylene oxide) amphiphilic graft copolymer (PE-g-PEO) that is a product of ethylene oxide ring-opening polymerization of an ethylene vinyl acetate copolymer having from 10 to 40 weight percent of vinyl acetate wherein the PE-g-PEO is according to Formula (I):

(I)

wherein R is hydrogen, alkyl, substituted alkyl, vinylic substituted alkyl, hydrocarbyl, substituted hydrocarbyl, or vinylic substituted hydrocarbyl group; the molar value of m is in the range from 2 to 40 mole percent; the molar value of n is in the range from 60 to 98 mole percent; and p is in the range from 5 to 500 ethylene oxide units.

14. The wound dressing film of claim 9, wherein the amphiphilic graft copolymer comprises a polypropylene-poly(ethylene oxide) amphiphilic graft copolymer (PP-g-PEO) that is a product of a polypropylene-maleic anhydride co-polymer (PP-MA) having from 10-50 weight percent of maleic anhydride wherein the PP-g-PEO is according to Formula (II):

(II)

wherein R is hydrogen, alkyl, substituted alkyl, vinylic substituted alkyl, hydrocarbyl, substituted hydrocarbyl, or vinylic substituted hydrocarbyl group; the molar percentages of grafted maleic anhydride units, m, is in the range from 2 to 10 mole percent; the molar values of propylene units, n, is in the range from 98 to 90 mole percent, and p is in the range of 5 to 500 ethylene oxide units.

15. A method of making a medical device comprising:
obtaining a polyethylene-poly(ethylene oxide) amphiphilic graft copolymer (PE-g-PEO);
combining the PE-g-PEO with a base polymeric formulation comprising a polyethylene and a poly(ethylene oxide) to form a blend, which comprises:
  the polyethylene in an amount in the range of about 50 to less than 70% by weight;
  the poly(ethylene oxide) in an amount in the range of greater than 25 to about 50% by weight;
  the PE-g-PEO in an amount in the range of about 0.01 to about 5.0% by weight;
forming a film from the blend; and
treating the film or the PE-g-PEO with a nitric oxide-releasing agent to convert end groups of a portion of the PEO such that the end groups are directly bonded to the nitric oxide-releasing agent;
wherein the film is both breathable and a microbial barrier.

16. The method of claim 15 wherein the film has an air permeability before sterilization in the range of about 3.5 to about 25 seconds per 100 cc according to Gurley Densometer Air Permeability Measurements and a percent permeation of less than 0.1%.

17. The method of claim 15, wherein the nitric oxide-releasing agent comprises a diazeniumdiolate.

18. The method of claim 15, wherein the PE-g-PEO is a product of ethylene oxide ring-opening polymerization of an ethylene vinyl acetate copolymer having from 10 to 40 weight percent of vinyl acetate, wherein the PE-Q-PEO is according to Formula (I):

(I)

wherein R is hydrogen, alkyl, substituted alkyl, vinylic substituted alkyl, hydrocarbyl, substituted hydrocarbyl, or vinylic substituted hydrocarbyl group; the molar value of m is in the range from 2 to 40 mole percent; the molar value of n is in the range from 60 to 98 mole percent; and p is in the range from 5 to 500 ethylene oxide units.

19. The film of claim 1, wherein content of the polyethylene, the poly(ethylene oxide), and the additive totals 100%.

* * * * *

UNITED STATES PATENT AND TRADEMARK OFFICE
CERTIFICATE OF CORRECTION

PATENT NO. : 11,111,362 B2
APPLICATION NO. : 15/711653
DATED : September 7, 2021
INVENTOR(S) : Jianbin Zhang et al.

It is certified that error appears in the above-identified patent and that said Letters Patent is hereby corrected as shown below:

In the Claims

Column 24, Line 6 replace "PE-Q-PEO" after "wherein the" and before "is" with "PE-g-PEO"

Signed and Sealed this
Twenty-eighth Day of June, 2022

Katherine Kelly Vidal
*Director of the United States Patent and Trademark Office*